(12) United States Patent
Boeke et al.

(10) Patent No.: US 8,616,072 B2
(45) Date of Patent: Dec. 31, 2013

(54) SYSTEM AND METHODS FOR SAMPLING MATERIALS

(75) Inventors: Jef D. Boeke, Baltimore, MD (US); Min Li, Lutherville, MD (US); Heng Zhu, Towson, MD (US); Shunyou Long, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 297 days.

(21) Appl. No.: 12/223,885

(22) PCT Filed: Feb. 13, 2007

(86) PCT No.: PCT/US2007/004139
§ 371 (c)(1),
(2), (4) Date: Aug. 9, 2010

(87) PCT Pub. No.: WO2007/095366
PCT Pub. Date: Aug. 23, 2007

(65) Prior Publication Data
US 2010/0294046 A1    Nov. 25, 2010

Related U.S. Application Data

(60) Provisional application No. 60/772,767, filed on Feb. 13, 2006.

(51) Int. Cl.
*G01N 1/00* (2006.01)

(52) U.S. Cl.
USPC ........................................ 73/863.11

(58) Field of Classification Search
None
See application file for complete search history.

(56) References Cited

U.S. PATENT DOCUMENTS

| | | | | |
|---|---|---|---|---|
| 4,293,578 A | * | 10/1981 | Stone | 426/332 |
| 5,267,490 A | * | 12/1993 | Howells | 73/863.52 |
| 5,361,528 A | * | 11/1994 | Peacock | 43/6.5 |
| 6,444,171 B1 | * | 9/2002 | Sakazume et al. | 422/65 |
| 7,022,528 B2 | * | 4/2006 | Avdeef et al. | 436/172 |
| 2003/0026732 A1 | | 2/2003 | Gordon et al. | |
| 2004/0014097 A1 | * | 1/2004 | McGlennen et al. | 435/6 |
| 2005/0188705 A1 | * | 9/2005 | Jones et al. | 62/86 |
| 2007/0014692 A1 | * | 1/2007 | Erb et al. | 422/82.11 |
| 2007/0105214 A1 | * | 5/2007 | Micklash et al. | 435/306.1 |

* cited by examiner

Primary Examiner — Robert R Raevis
(74) Attorney, Agent, or Firm — Johns Hopkins Technology Transfer

(57) ABSTRACT

Provided herein are systems and methods for storage, retrieval and sampling of materials.

23 Claims, 7 Drawing Sheets

IcePick System Control Schematics

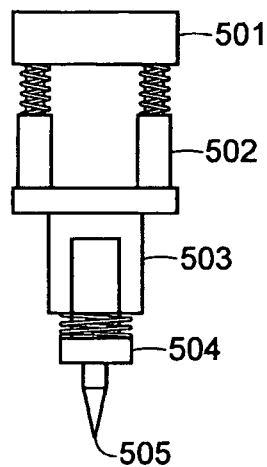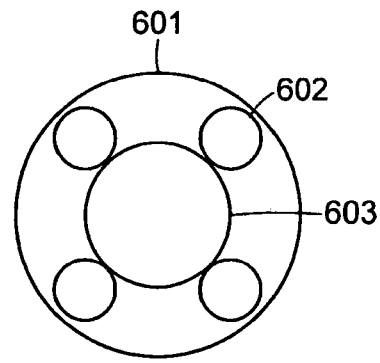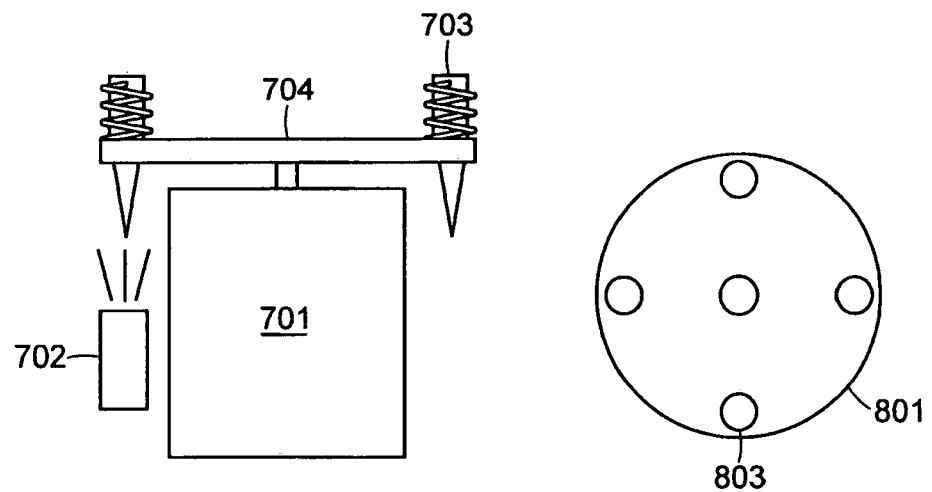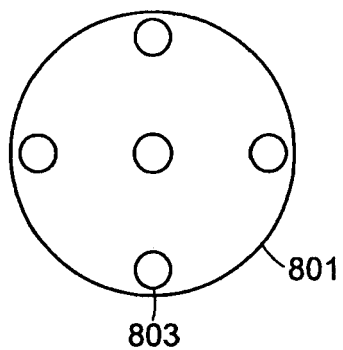
FIG. 5   FIG. 6
FIG. 7   FIG. 8

SYSTEM AND METHODS FOR SAMPLING MATERIALS

RELATED APPLICATIONS

This application claims the benefit of U.S. Provisional Application No. 60/772,767, filed on Feb. 13, 2006, which is incorporated herein by reference in its entirety.

BACKGROUND

Large biomaterial and chemical library collections require precise and selective access to a subset of material under sterile conditions. The materials are often stored in multiwell plates at low temperature where each individual sample is stored in one of the compartments or wells. The format of multiwell plates include, for example, 96 and 384 wells as well as other formats. Sample plates have an ensemble of wells with a registered position for each well. Such ensembles of wells may be physically linked or in a separable rack. The ability to access large subsets of these materials with precision and without cross-contamination and to avoid thawing is important to maintain the integrity of samples and material collections, which may be of limited supply. In addition, there is also a need in the art to have a system that can, without human intervention, access a subset of the wells in a collection of source plates, take a portion or all of a sample, and re-array the sample into a destination plate(s) according to need.

SUMMARY

The present invention provides methods to store, retrieve, and sample a subset of frozen biological and other material (e.g., drug and candidate drug substances) while minimizing contamination and/or damage to surrounding samples. It further describes an integrated system that allows efficient management of large, complex libraries of biomaterials or other substances.

In one aspect, provided herein are systems for retrieving a subset of a stored sample, comprising an automated freezer comprising a dispenser, a climate controlled receiving chamber adjacent to the dispenser, a transfer device (plate handler) within the receiving chamber, and an addressable sampler (picking robot).

In one embodiment, the dispenser communicates with the climate controlled receiving chamber through a port.

In one embodiment, the addressable sampler comprises a tip.

In another embodiment, the tip comprises a metal tip with high thermal heat capacity, metal pin, a ceramic pin, a hollow pin, a core sampler for retrieving a portion of a sample In another embodiment, the tip comprises a tip head. In another related embodiment, the tip is disposable. In another related embodiment, the tip comprises a volume control mechanism.

In one embodiment, the system further comprises a heat sensor to monitor the temperature in the vicinity of the tip.

In one embodiment, the addressable sampler comprises one or more of a sample locator, a rotating tip station for maintaining sampling tips at a sampling temperature, an addressable sample picker.

In one embodiment, the sample locator comprises a barcode reader.

In one embodiment, the system further comprises a delidder (delid slide).

In one embodiment, the system further comprises a tip sterilizer.

In one embodiment, the system further comprises one or more destination plates for receiving retrieved samples.

In one embodiment, the automated freezer is a vertical or horizontal storage freezer In one embodiment, the climate controlled receiving chamber comprises one or more of a humidity controller, an atmospheric gas control mechanism or a reading device to identify the containers as they are inserted into and retrieved from the chamber.

In one embodiment, the transfer device comprises a mechanism to transport a sample tray between the dispenser and the addressable sampler.

In one embodiment, the system further comprises a controller in communication with one or more of the automated freezer, the dispenser, the transfer device or the addressable sampler.

In one embodiment, the controller monitors one or more of the freezer, the transfer device, or the sampler.

In another embodiment, the controller receives and processes orders from at least one user.

In one embodiment, the controller comprises a processor for processing data relative to a sample being stored in and retrieved from the system.

In another embodiment, the controller performs at least one of the following functions: advising a user of sample availability, advising of sample delivery date to the dispenser, monitoring an amount of sample within the dispenser, informing a supplier of sample purchased by a user and requesting the supplier to provide additional items to replace items dispensed from the dispenser.

In one embodiment, a supplier communicates with the dispenser via the central controller.

In one embodiment, the system further comprises a communication network for providing communication between the controller and at least one user and at least one supplier.

In one embodiment, the communication network is selected from the group consisting of: an intranet, an Ethernet, an Internet, a telephone network, a wireless network and a combination thereof.

In one embodiment, the controller comprises a computer.

In one embodiment, the system further comprises a climate system for controlling the climate of the climate controlled chamber.

In one embodiment, the climate system comprises a dry gas supply to dehumidify the chamber and/or cool the chamber.

In another embodiment, the dispenser is configured to interchange a sample container between the dispenser and the climate controlled receiving chamber while in a chamber exchange position, and interchange a container between the dispenser and the transfer device while in a transfer exchange position.

In one embodiment, the transfer device is configured to deliver the container to the addressable sampler.

In another embodiment, the chamber further comprises a transporter to transport a sample from the dispenser to the sampler.

In another embodiment, the chamber comprises one or more of a reading or writing device.

In one embodiment, the reading device is configured to identify the sample.

In one embodiment, the sample is contained in a sample plate containing other samples.

In one embodiment, the sample plate comprises a 96 or a 364 well sample plate.

In one embodiment, the system further comprises a control system, wherein the control system is operatively connected with the carousel, the interchange mechanism, and chamber for controlling their operations.

In one embodiment, the system further comprises a user station operatively connected to the apparatus, the user station comprising a data input means for inputting data to the processor relative to the containers.

In one embodiment, the system further comprises a destination plate handler module adapted to transport destination plates to a destination.

In one embodiment, the destination comprises one or more of a freezer, a refrigerator, an incubator, a hood, or a climate controlled environment.

In one embodiment, the system further comprises a plate queuing system.

In one aspect, provided herein are methods for sampling a frozen sample, comprising retrieving a sample in a container from a freezer, transferring the sample to an addressable sampler, and sampling the sample and transferring the sample to the freezer.

In one embodiment, the method further comprises delidding a sample plate in a climate controlled chamber In one embodiment, the method further comprises determining the location of the sample in the container prior to sampling.

In one embodiment, retrieving the sample comprises ejecting the container to an exterior of the freezer for transport to an addressable sampler.

In one embodiment, sampling comprises transiently thawing at least a portion of the sample.

In another embodiment, the sample rapidly refreezes upon return to the freezer. In one embodiment, the container comprises a multiwell plate.

In another embodiment, adjacent samples to the sample being sampled are not thawed.

In one embodiment, the method further comprises sealing the container with a seal prior to freezing in the freezer a first time.

In another embodiment, the seal comprises a foil seal, a plastic seal, a polymer seal or a septum.

In one embodiment, the method further comprises placing a lid on the sealed container prior to freezing the sample before and/or after sampling.

In one embodiment, the method further comprises transferring the portion of the sample to a destination plate.

In one embodiment, the method further comprises sampling one or more further samples from the container.

In one embodiment, the method further comprises transferring each of the one or more further samples to a destination plate.

In one embodiment, the freezer comprises a Biophile and or a Biobank.

In another embodiment, sampling comprises lowering a heated pin through the seal of the container and into the frozen sample, wherein at least a portion of the sample is thawed.

In another embodiment, sampling comprises lowering a coring pin or coring saw through the seal of the container and removes a portion of the frozen sample.

In one embodiment, the method further comprises sterilizing the pin between sampling.

In another embodiment, the pin is disposable.

In another embodiment, the pin comprises a temperature of between about 30 and 70° C.

In one embodiment, once partial or full thawing occurs, the pin is removed from the source well and dipped into the destination well, releasing a sample of cells.

In one embodiment, the tip is sterilized between retrieving samples.

In another embodiment, sterilizing comprises scrubbing the pin in a brush bath, dipping the pin into a series of wash baths, or heating the pin to a sterilization temperature.

In another embodiment, sterilization temperature comprises from between about 121° C. to about 500° C.

In one embodiment, a pin comprises one or more of a penetrating device permitting contact with material in the mentioned compartment, wherein the pin is one or more of hollow, solid, or slotted.

In one embodiment, the method further comprises monitoring the temperature of the tip.

In another embodiment, the tip comprises a volume control mechanism. In another embodiment, sampling comprises replicating a sample plate.

Other embodiments are disclosed infra.

BRIEF DESCRIPTION OF THE DRAWINGS

FIG. 5 depicts a side view of a component of one embodiment of an addressable sampler.

FIG. 6 depicts a top view of a component of one embodiment of an addressable sampler.

FIG. 7 depicts a side view of a component of one embodiment of an addressable sampler component, e.g., a rotating tip station.

FIG. 8 depicts a top view of a component of one embodiment of an addressable sampler component, e.g., a rotating tip station.

DETAILED DESCRIPTION

Figure 1:
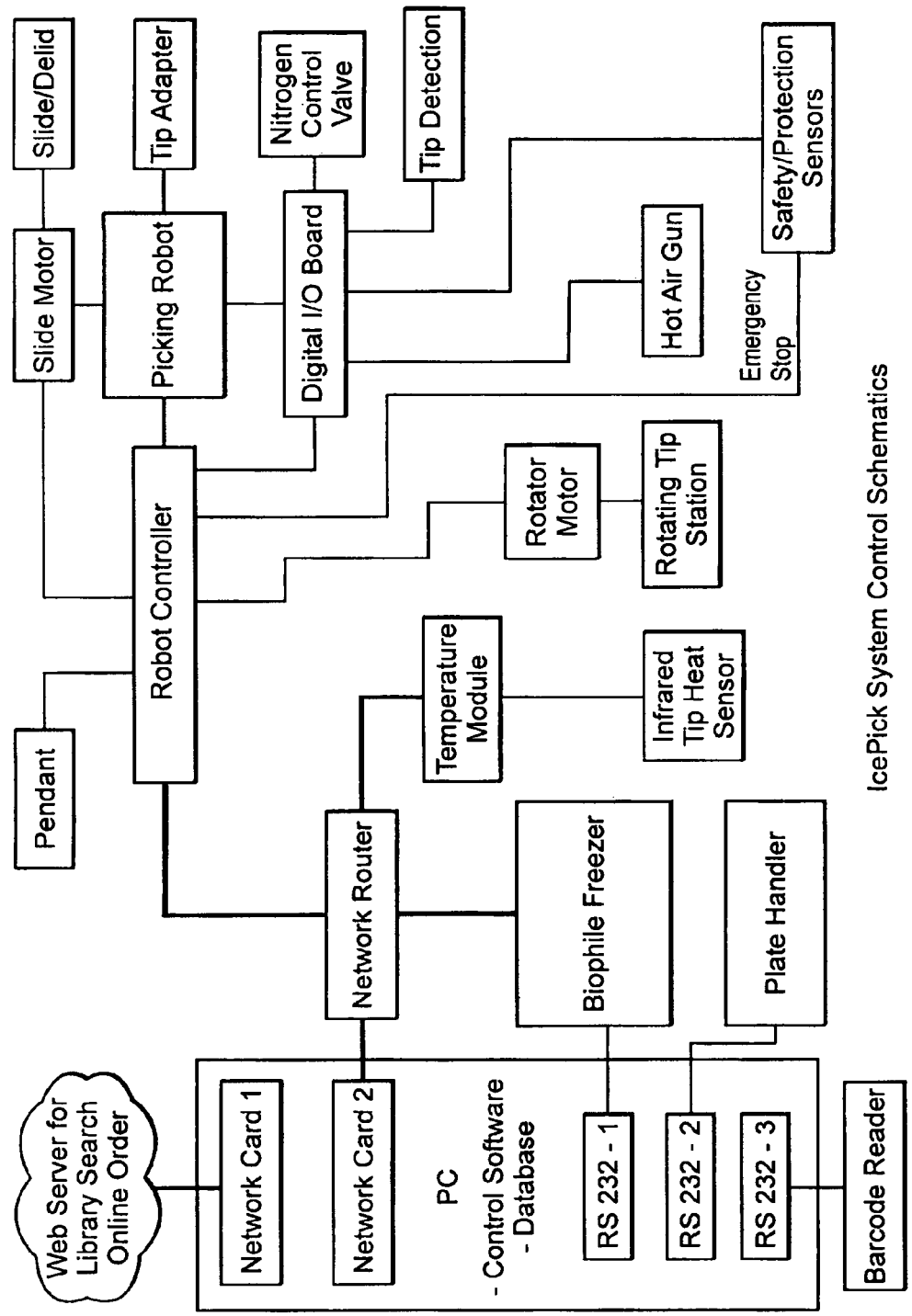
FIG. 1 is a flow chart of an exemplary system.

The presented herein is an automated storage and retrieval apparatus, and related method thereof, providing a sample process management system to the store and retrieve samples. Samples in containers are stored and retrieved automatically through a dispenser (e.g., an airlock climate-control chamber (access means)) that is automatically dehumidified by a dry gas purge (e.g., carbon dioxide or nitrogen purge or the like). This purge rapidly reduces ambient humidity to a desirable relative humidity (RH), (e.g., less than about 15% RH), to minimize or eliminate the accumulation of frost on the sample plates. Microplates or storage containers, or the like, are identified, for example, using barcode technology or radio frequency technology. The containers containing the samples are transferred by the transfer device to the addressable sampler where they are sampled using pins or other described means. The sample containers or plates are then transferred back to the freezer via the transport device (e.g., a rotary mechanism) through the dispenser. The freezer transports the containers to a derived location for example by use of a carousel to one of the stationary addresses. For illustrative purposes only, the carousel and stationary nests may have a combined capacity of 1,000 standard microplates. It is contemplated that various capacities may be designed.

An advantage of the present invention operation in a stand-alone mode or can be integrated into a completely automated laboratory. The systems are scalable to meet the needs of small laboratories as well as large institutions that require long-term storage of large numbers of samples. Another advantage of the present invention is that the apparatus can be designed as a slide-in unit for existing ultra-cold freezers, which will keep the majority of the hardware in the door so as to be insulated from the freezer compartment, minimizing both the number of low-temperature hardware components and the actual alteration to the freezer itself. However, the freezer, as described herein, may be altered to accommodate additional features of the systems. A reduced number of moving components continuously exposed to the design temperature of about −80° C., which reduces the cost of production.

Further advantages of the present invention are attributed to the improved sample quality, lowered operating costs, accuracy of clone picking and reduced maintenance of the automated storage and retrieval apparatus.

In one embodiment, the dispenser comprises at least one rotatable carousel located in the freezer, the carousel comprising at least one cell defined by two side walls each side wall extending from a central location of the carousel, an access hatch aligned with the or each carousel for accessing an interior of the at least one cell; and a motor for rotating the carousel.

In one embodiment, the controller performs at least one of the following functions, rotation of the carousel by controlling the motor, controlling dispensing of an item from the dispenser, monitoring an amount of an item within the dispenser, reporting to the central controller the amount of an item within the dispenser, making an activity log and temperature log of the dispenser, informing a user of availability of an item, receiving information from the central controller in relation to item delivery to the dispenser and temperature control setting of the dispenser and monitoring and controlling an internal environment of the dispenser.

In one embodiment, the controller comprises a computer. More than one controller may be associated with the system and may control discrete functions. All or any subset of functions may be controlled by one controller. In some embodiments, the control system comprises a processor for processing data relating to contents of the containers being stored in and retrieved from the apparatus.

In one embodiment, the system further comprises a user station operatively connected to the system, the user station comprising a data input means for inputting data to the processor relative to the samples or the sample containers.

In one embodiment, the system comprises a plate queuing system allowing the freezer to unload one or more additional plates while a plate is being sampled. The queuing of the sample plates will allow for higher throughput of retrieving samples. The queuing of sample plates may be just after being dispensed from the freezer, before or after being delidded (for lidded sample plates), or in-line for the sampler. The queuing system may also be in the freezer compartment or in a freezer compartment operably linked one or more of the freezer, the climate controlled receiving chamber, the transfer device or the sampler.

In one embodiment, methods for automatically sampling a stored sample from a frozen sample plate comprises providing a carousel in the freezer compartment; depositing a container into a climate-controlled chamber; controlling the climate of the chamber while the container remains in the chamber; sampling one or more samples, and returning the container to the freezer carousel.

In certain embodiments, exemplary freezers include, for example, the Biophile (TekCel) and the Biobank (Thermo Systems).

Described herein are methods to store and efficiently retrieve a subset (e.g., user-defined) of biological materials (e.g., viruses, bacteria, yeast, fungi, sperm, worms, mammalian cells, plant tissue, animal tissue) from a freezer (e.g., source compartment). The methods and systems described herein reduce contamination of the sample and mistakes in sampling biological samples while increasing efficiency. Portions of the samples (e.g., the inoculum, dispensed biomaterial, sampled material, portion of sample) may be placed into a destination compartment or plate for further processing or storage.

In certain embodiments, the dispensed biomaterial to be managed or retrieved is, for example, placed in a sample plate (e.g., single well, 2 well, 3 well, 6 well, 16 well, 96 well, 384 well plate, 1536 well plates) sealed with a foil (e.g., aluminum, gold, tin, etc.) or polymer (plastic, rubber, etc.) seal and covered by a plastic lid prior to the storage. This lid is removed to allow access by the addressable sampler (e.g., picking robot). Retrieval of a collection of materials in pre-sealed plates (e.g., source compartments) is performed by a penetrating pin from the top of the 96 or 384 or 1526-well plate at a given well position. The pin of the addressable sampler may contain a slot or other recess to facilitate uptake of a small sub-sample of liquid from the well. The position may be registered manually or, for example, by robotics controlled by a computer. The penetration of the pin through the foil seal permits contact between the tip of pin and the compartmented material, either in solid (frozen) or liquid form. Methods for thawing a frozen sample are described herein. The retrieval of the pin and sample contained therein or thereon comprises the retrieved sample. The pin may then be inserted into a bio-compatible sample compartment (e.g., into a specified or random well of a "destination plate") to transfer sample on or in the pin.

In one embodiment, the methods comprise withdrawing a small sample (liquid or solid) from a well containing a frozen biomaterial, (e.g., stored at or around −80° C.). The sample is withdrawn under sterile conditions, in a short period of time (shorter than user manual selection of a sample from a sample plate), and transfer a portion of the sample to a destination well (e.g., containing growth medium).

The methods are accomplished by the systems described herein, for example, by an addressable sampler (e.g., a robotic arm system that lowers a precision-heated (temperature-controlled) pin through the seal of a sample and into the frozen sample block. The pin is heated to a predetermined temperature warm enough to melt a portion of or the entire block of material in that compartment but not warm enough to harm the materials (in certain embodiment, or affect neighboring sample in the sample plate). The temperature or temperature range for a particular sample is easily determined empirically by one of skill in the art. The pin, for example, rests in a thermostatically controlled heating block or a rotating tip station, that can be warmed precisely to the desired temperature; heat travels through the pin and into the sample by conduction. Exemplary pin tip temperatures are, for example, between about 30 and about 70° C. Once partial or full thawing occurs, the pin is removed from the source well and dipped into the destination well, releasing a sample of cells which can subsequently be grown and used for many purposes, e.g., preparation of nucleic acid, PCR, bioassays etc.

After sampling, the source compartment rapidly refreezes due to the low temperature of biomaterials in adjoining wells and also by returning the sample plate to the freezer. Thus sample integrity is maintained.

After delivering the inoculum, the pin may be cleaned and sterilized before reuse. In one embodiment, the pin is disposable. For reusable pins, there are many well-known methods for sterilizing the pin, e.g., scrubbing the pins in a brush bath, sonicating, dipping the pin into a series of wash baths, and/or heating the pin to an extremely high temperature.

In certain aspects, the system comprises an automated freezer (e.g., robotic freezer (e.g., Biophile)), a transfer device (e.g., plate transfer robot (e.g., Twister 2)), an optional delidding device (e.g. robotic arm to remove the lid, e.g., modified from motorized slide), a climate controlled receiving chamber containing the transfer device and optionally the delidding device, and an addressable sampler (e.g., robotic arm or gantry system modified to hold heated pin device (e.g. Adept Cobra)), and a controller (e.g., computer to integrate the components of the system (e.g., the heating/temperature controlling system, provide a user interface to operate the system). In one embodiment, the system further comprises a destination plate module (e.g., a robotic arm and plate hotel to move destination plates to, for example, a heated incubator).

Exemplary freezers include for example, a Biophile automatic freezer, which holds 931 96- or 384-well plates. The Biophile can therefore organize up to 357,504 samples. The freezer is adapted to retrieve or return any of the 931 plates in about 30 seconds. In one embodiment, the system comprises more than one source freezer.

As used herein, biomaterial includes, for example, microbial prokaryotes or eukaryotes, cells, viruses, the components of cells, components of viruses, or component tissues or organisms.

The systems described herein are useful for managing collections of bacteria (*Escherichia coli*), retroviruses, bacteriophages or other recombinant viruses and yeast (*Saccharomyces cerevisiae*) for various purposes, and of chemical compound libraries, and frozen tissue micro-samples/homogenates.

As used herein, a component of the sampler is the pin, which includes, for example, a penetrating device that permits contact with material in the mentioned compartment with biomaterials; pins can be hollow, solid, slotted or have other types of recesses designed to adhere to droplets of liquid. The tips may be heated passively (hot air, heat block) or actively (by conduction). The temperature of the tip may be monitored by a real-time temperature monitoring system by incorporating a thermostat, allowing more precise temperature control. A thermistor may also be imbedded in the tip to provide real-time monitoring on intra-tip temperature. In certain embodiments, sterilized disposable arrayed tips or individual tips are used. The tips may also have liquid volume control mechanisms (e.g., pipetting). For example, constant volumes of frozen samples could be picked up and delivered by the system, for example by employing a hollow picking pin, connected to a liquid volume control (e.g., pipetting) module. The tip may also be a core sampling device to core a frozen samples, e.g., without thawing the sample. For example, a rotating coring tip could cut/drill sample from a tissue slice or other frozen material without thawing it.

In one embodiment, the system allows object sampling followed by freezing of the samples by adding visual devices to identify randomly positioned objects. For example, this would allow microbial colonies grown on an agar plate (and randomly or non-randomly placed) to be samples and the samples frozen.

In one embodiment, a plate handler replaces used plate lids to avoid ice buildup on source plates, which is problematic. In one embodiment, the lids are coded to be read by the reading device. In other embodiments the sample plates are coded.

In one embodiment, the system further comprises a destination plate handler. The destination plate handler may delid and relid destination plates and transfer them to a "plate hotel", refrigerator, freezer or other incubation station.

In one embodiment, low profile 96-well (Genetix X 6011) or 384-well (Genetix X7001) plates with or without samples are stored in the freezer with the plastic lid on.

The system, in one embodiment, stores samples (e.g., plasmid libraries in bacterial cells, yeast knockout collections, etc.) in a −80 C automatic freezer (BSU; BioPhile), loads and unloads plates to and from the freezer, and picks individual isolates from frozen (source) plates to destination plates.

The system is adapted to transfer samples from, for example, individual sample containers, 96-well to 384-well or 384-well to 96-well format with 96-pin (Genetix X5054), the system is also adapted to replicate plates (e.g., replicate from 384-well to 384-well with 200 nl pin tool).

In certain embodiments, the system includes, for example, the following components: 1) Biophile BSU automatic freezer; 2) Adept Cobra s600 robot (component of the plate transfer device); 3) Zymark Twister II for plate handling (component of the plate transfer device); 4) Animatics Smart motor 1 for rotating tip station (component of the addressable sampler); 5) Yamaha slide for plate transfer and delidding (additional optional component of the plate transfer device if the plate has a lid); 6) Animatics Smart motor 2 for plate transfer (component of the plate transfer device); 7) IBM PC (referred to as the central or controlling PC); 8) Cisco router for networking; 9) Advantech temperature test module; 10) HAKKO 852 hot air gun (component of the addressable sampler); 11) Custom control console.

Software

The System adopts a "distribution control" concept. The System software package integrates a variety of commercial control software packages associated with off the shelf components, for example, 1) system software; 2) Biophile GenOne software which runs on the flat panel PC on the BioPhile freezer. User can operate the freezer through a touch screen when the System software package is not activated. There are 2 channels connecting the panel PC to the central PC. One is TCP/IP used for database management. Another is an RS-232 interface allowing the System Software package to send commands for loading/unloading plates to/from the BioPhile; and/or 3) Adept robot software which is executed by the SmartController. It communicates with PC through TCP/IP networking; 4) Two pieces of Software for the Animatics Smart motors. They are downloaded to the motors. They connect to the Adept robot through SmartController RS-232 ports. There is no direct control from the System software package to the smart motors and/or 5) Hit list preprocessing software. This is another piece of custom software currently consisting of a Microsoft Excel macro which loads the template plate order sheet and generates the hit list for robot.

Figure 2:
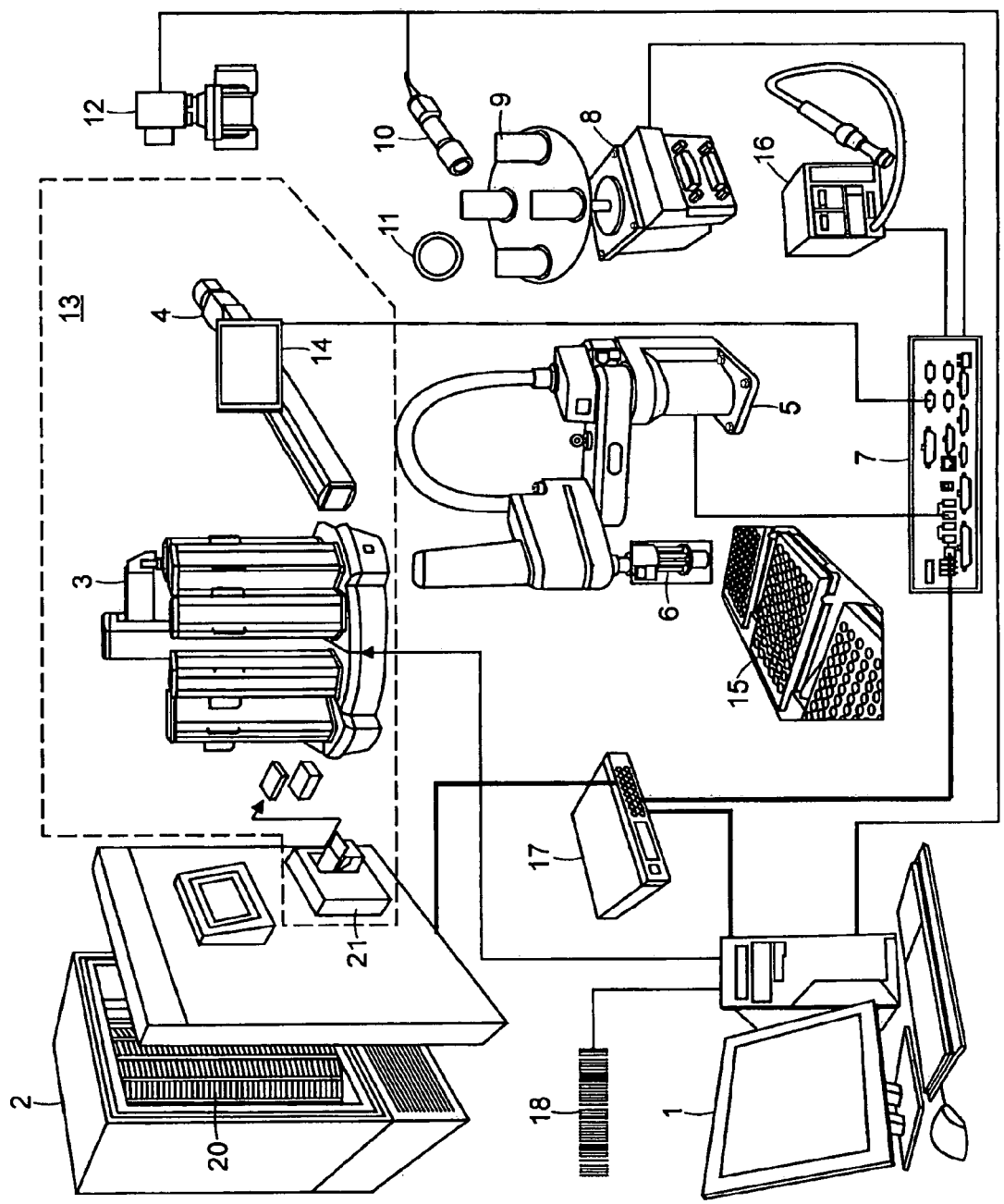
FIG. 2 is a schematic of an exemplary system showing an automated freezer with dispenser, a transfer device (plate handler), the addressable sampler (picking robot, tip, tip heater, temperature sensor), the controller, destination plates and reader device.

Turning now to the drawings, the present invention is schematically shown in the plan view of FIG. 1 and perspective view of FIG. 2, which includes an automated storage and retrieval apparatus having one or more storage carousels 20 disposed in an automated freezer 2, with one or more optional stationary racks, a climate controlled receiving chamber (13, N2 environmental chamber), a transfer device 4. The climate controlled receiving chamber 13 is generally disposed on a wall 11 of the freezer 2. A control system 1 is coupled to the reading device 18 (e.g., barcode scanner), the addressable sampler (components 5, 6, 8, 9, 16), transport device 4, and climate controlled chamber 13 for controlling their operations. Generally, the control system 1 controls the operation of the apparatus so that the containers 14 can be loaded from the exterior or sampling position into the climate-controlled chamber 13 for retrieval by the transport device 4 and the plate handler 3 to dispensing port 21 for insertion onto the carousel 20 in the freezer 2. Stored containers subsequently can be retrieved from the carousel 20 the plate handler 3 and by the transport device 4 and available to be taken to the sampler (components 5, 6, 8, 9, 16).

Figure 3:
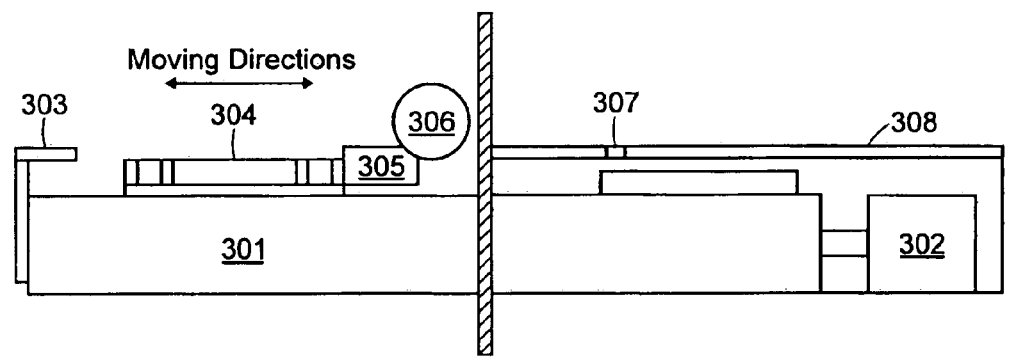
FIG. 3 depicts a side view of a component of one embodiment of a transfer device.

FIG. 3 shows a side view of a component of one embodiment of a transfer device. A sample container (plate) is dispensed from the freezer through the dispenser (shown as 21 in FIG. 2) and in one embodiment taken by a robotic arm to the transport mechanism 4. The transport mechanism comprises a slide 301 a reading device 305, a guide wheel 306 to properly locate the plate, a cover 308 with a tip access slot 307, and a motor to drive the operations. The transport device is controlled by the controller. In certain embodiments, the robotic transport arm may be a conveyer belt operably coupled to the dispenser and the transport device may be integral. The transport device may be located within or outside of the climate controlled receiving chamber. The receiving chamber surrounds the dispenser of the freezer.

Figure 4:
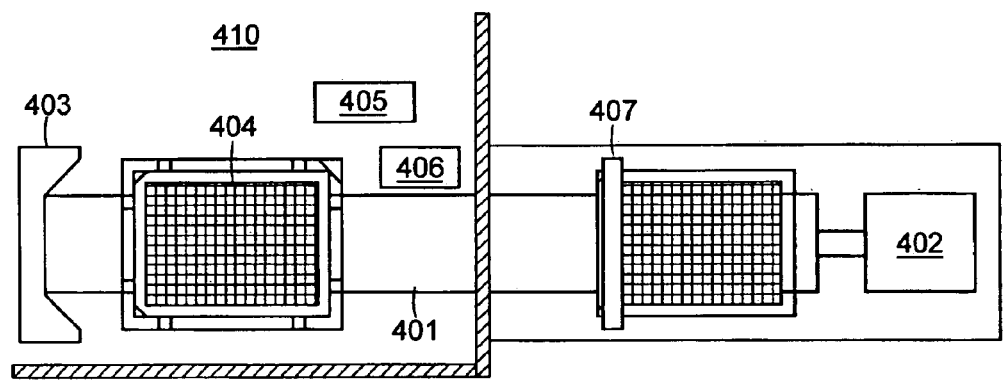
FIG. 4 depicts a top view of a component of one embodiment of a transfer device.

In regard to FIG. 4, depicted is a top view of a component of one embodiment of a transfer device as shown in FIG. 3. The sample plate 404, is shown on the slide 401, and is transported to the tip access slot 407 by the controller so that the proper sample in the plate may be accessed by the addressable sampler. The addressable sampler has access to the sample through the tip access slot 407.

FIG. 5 depicts a side view of a component of one embodiment of an addressable sampler, the tip 505 and related assembly. In this embodiment, the tip is passively heated by a hot air gun and no heating assembly is included. In some embodiments, a heating assembly is included in the tip assembly. The tip assembly as shown comprises a magnetic tip holder 503, a spring compensator 502, and an adapter 501. FIG. 6 depicts a top view of a component of one embodiment of an addressable sampler, adapter 601 with four spring compensators 602. FIG. 7 depicts a side view of a component of one embodiment of an addressable sampler, e.g., a rotating tip rack 704 and the heater 702. The tip rack 704 is rotated by a motor 701 so that each tip is exposed to hot air from the hot air nozzle 702. The tips are rotated every 1 s to 2 minutes, depending on the temperature desired for sampling.

FIG. 8 depicts anther top view of a component of one embodiment of an addressable sampler, e.g., a rotating tip station, the tip rack 801 with four positions for tips 803.

It is envisioned that a control system and computer system can be accessed directly by using the touch screen interface and/or remotely by a stand-alone personal computer or with a local area network (LAN).

Figure 9A:
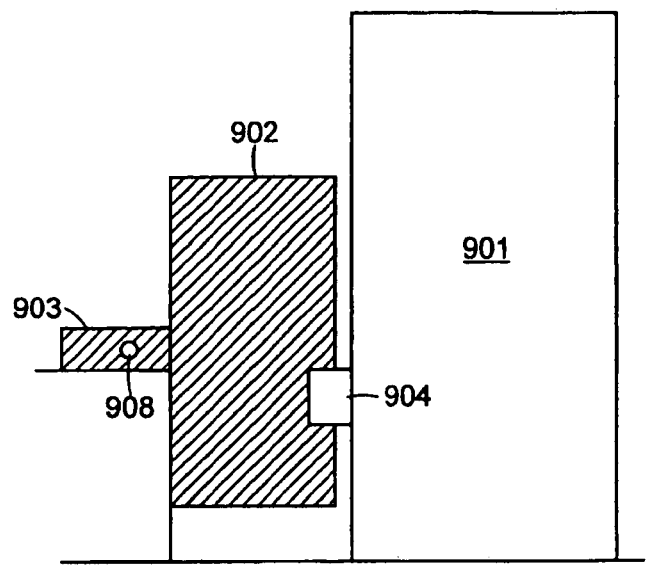
FIG. 9A depicts a side view of a component of one embodiment of a climate controlled receiving chamber.
Figure 9B:
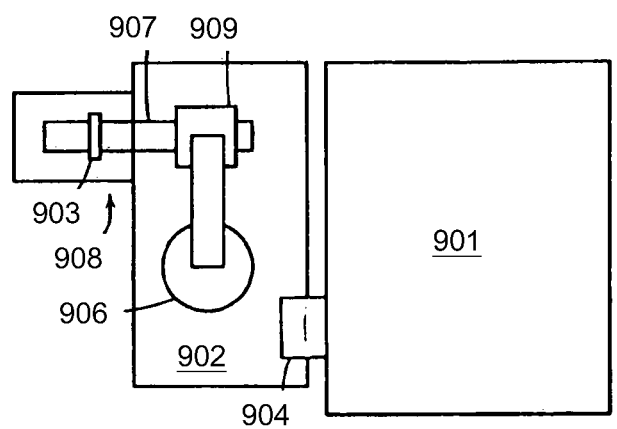
FIG. 9B depicts a top view of a component of the embodiment of the climate controlled receiving chamber illustrated in FIG. 9A.

Next, details of the climate controlled receiving chamber will be provided, as best shown in FIGS. 9A and 9B. A particularly desirable feature is that the climate-controlled chamber 902 prevents ambient, humid air from entering the interior of freezer compartment 901 during storage container insertion and retrieval. The receiving chamber 902 encompasses the dispenser 904 to allow communication between freezer 901 and receiving chamber 902, and an exterior door 903 to allow communication between the exterior environment (or adjacent area) and chamber 901. The chamber 901 has a climate control system 908 that provides an air purging capability to dehumidify and optionally cool the air in the chamber 902 before dispenser 904 is opened. A scanning reader device 935, preferably a barcode reader, is situated in the chamber 902 to identify storage containers as they are inserted into and retrieved from chamber 902. Information relative to the storage containers is transmitted from reader device to central and/or remote processor.

Referring to FIG. 9B the storage containers 909 are carried by a transfer device 907 to the addressable sampler (picking robot). The transfer device 907 can transport the container 909 to the exterior as the exterior door is open. Alternatively, the transfer device 907 can transport the container 909 to the interior of the freezer through the dispenser. A climate control system 908 is in communication with the receiving chamber 902 that dehumidifies and optionally cools the chamber 902 while the container is isolated therein, e.g., both exterior and interior doors are closed. The climate control system 908 includes a dry gas or dry air purge (e.g., nitrogen, carbon dioxide, or the like), that rapidly reduces ambient humidity to any desired level, e.g., less than about 25% relative humidity (RH) and as low as about 1% RH. In fact, any compressed gas from which moisture has been removed will reduce the humidity in the airlock, and will cool the airlock by adiabatic expansion to about $-10°$ C. to about $0°$ C., or as desired.

Preferred embodiments of the present invention, an automated storage and retrieval apparatus, and related method thereof, operate at an ultra low temperature from about $-50°$ C. to about $-90°$ C. It should be understood that the apparatus may operate in a range of $-50°$ C. up to ambient temperature or greater. The normal design operating temperature of the freezer compartment of the present invention is about $-80°$ C. It should be noted that the present invention is contemplated to operate at conditions colder than ultra low temperatures in the range of about $-140°$ C. to about $-90°$ C. Conveniently, if the freezer fails for whatever reason—maintenance or scheduled outage—then liquid carbon dioxide can be pumped into the system and keep it at approximately $-78°$ C. Thus, the ultra low freezer-set point of the apparatus can be backed up by installing a cylinder of liquid carbon dioxide.

One skilled in the art would appreciate that various types and substitutes for interior and exterior chamber doors can be used. Moreover, a single door can be utilized which can rotated between interior and exterior sides.

With regards to control operations, the present invention automation and robotic motions described herein are provided in part by the control system and processor. It should be noted that the following exemplary sequences of operations may be varied, partially omitted, overlapped to reduce the total elapsed time of operation, or reordered in an alternative sequence.

Operation for depositing a storage sample tray is provided as described below. In a first step, the dispenser of the freezer opens and the sample tray exits into the climate controlled chamber. The lid of the tray is removed and the transfer device transports the tray to the addressable sampler through the exterior door of the climate controlled chamber. Once sampled, the transfer device transports the tray back to the dispenser for placement back in the freezer. The reading device of the system may be located in the climate controlled receiving chamber or associated with the addressable sampler or both.

In one embodiment, a central controller locates relevant storage container information in the database and location of storage container in the freezer (or stationary storage racks) is determined. Optionally, if security is required, then an access code is entered via data input device such as a display panel integral with the apparatus housing or a remote processor, and confirmed by central processor 81 to allow access to the desired storage container. The container is ejected from the freezer through the dispenser.

It should be noted that the motors for the freezer, transfer device, the addressable sampler and can be a variety of types of motors known to those skilled in the art, including but not limited thereto servo motors and stepper motors, or any direct current (DC) motor with suitable position or velocity controllers. In the various preferred embodiments disclosed herein, the motors are mounted outside of the freezer to extend the life of the component and improve the overall serviceability of the apparatus. In one embodiment, the servomotors may be of a SMART MOTOR by Animatics, Corp. These types of servo motors are microprocessor controlled, ensuring accurate placement and monitoring of the robotics operating within the critical environment; however, any position or velocity controlled motors may be used. Motors are mounted near the particular component they are controlling.

The general features of the present invention control system will be discussed, as shown in the block diagram of FIG. 1. The control system interfaces with a computer system that may be integral with the housing or remote via a wire or wireless communication, or any combination thereof. Moreover, the control system may be in communication with and integrated with a laboratory information management system (LIMS). The control system is operatively connected with the various motors, actuators, position sensors, and identification sensors. It is contemplated that that the information derived from the sample or work pieces carried in the containers while practicing the present invention will provide an information technology platform for the user. The computer system is intended to be a user-friendly, utilizing Windows-based platform or any other operating system, and may be integrated with a variety of laboratory information management systems. It is envisioned that the control system and computer system can be accessed directly by using a touch screen interface or remotely by a stand-alone personal computer or with a local area network (LAN).

The present invention apparatus provides the user the capability, among other things, to set top-level user-definable parameters to control container (sample) access based on research groups, research campaigns or individual laboratories. For instance, sample data can be configured by the user to meet the user's particular research requirements. The database can then search the user's sample populations to find all the samples that match the user's requested research parameters. Moreover, time/temperature profiles and sample access histories are maintained continuously. The present invention allows the user to set sample migration thresholds. This feature, employing sample usage frequencies, prompts the movement of low demand samples into longer-term storage units—maximizing the efficiency of the user's sample process management system. Furthermore, the present invention apparatus enables the user to generate a variety of reports in support of the user's quality assurance needs. Finally, the user will benefit from the present invention's information technology by receiving excellent sample security, optimal sample visibility, optimal quality assurance, sample migration control and flexible data management.

The controls and processing of present invention may be implemented using hardware, software or a combination thereof and may be implemented in one or more computer systems or other processing systems, such as personal digit assistants (PDAs). In an example embodiment, the invention was implemented in software running on a general purpose computer. Computer system includes one or more processors in a communication infrastructure (e.g., a communications bus, cross-over bar, or network). Computer system includes a display interface that forwards graphics, text, and other data from the communication infrastructure (or from a frame buffer not shown) for display on the display unit.

The computer system may also include a main memory, preferably random access memory (RAM), and may also include a secondary memory. The secondary memory may include, for example, a hard disk drive and/or a removable storage drive, representing a floppy disk drive, a magnetic tape drive, an optical disk drive, etc. The removable storage drive reads from and/or writes to a removable storage unit in a well known manner. Removable storage unit, represents a floppy disk, magnetic tape, optical disk, etc., which is read by and written to by removable storage drive. As will be appreciated, the removable storage unit includes a computer usable storage medium having stored therein computer software and/or data.

The computer system may also include a communications interface. Communications interface allows software and data to be transferred between computer system and external devices. Examples of communications interface may include a modem, a network interface (such as an Ethernet card), a communications port, a PCMCIA slot and card, etc. Software and data transferred via communications interface are in the form of signals, which may be electronic, electromagnetic, optical or other signals capable of being received by communications interface. Signals are provided to communications interface via a communications path (i.e., channel). A channel (or any other communication means or channel disclosed herein) carries signals and may be implemented using wire or cable, fiber optics, a phone line, a cellular phone link, an RF link and other communications channels.

In this document, the terms "computer program medium" and "computer usable medium" are used to generally refer to media such as removable storage drive, a hard disk installed in hard disk drive, and signals. These computer program products are means for providing software to computer system. The invention includes such computer program products.

Computer programs (also called computer control logic) are stored in main memory and/or secondary memory. Computer programs may also be received via communications interface. Such computer programs, when executed, enable computer system to perform the features of the present invention as discussed herein. In particular, the computer programs, when executed, enable processor to perform the functions of the present invention. Accordingly, such computer programs represent controllers of computer system.

In an embodiment where the invention is implemented using software, the software may be stored in a computer program product and loaded into computer system using removable storage drive, hard drive or communications interface. The control logic (software), when executed by the processor, causes the processor to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software. In an example software embodiment of the invention, the methods described above were implemented in VISUAL BASIC control language, but could be implemented in other programs such as, but not limited to, C++ programming language.

The invention may be embodied in other specific forms without departing from the spirit or essential characteristics thereof. The foregoing embodiments are therefore to be considered in all respects illustrative rather than limiting of the invention described herein. Scope of the invention is this indicated by the appended claims rather than by the foregoing description, and all changes which come within the meaning and range of equivalency of the claims are therefore intended to be embraced herein.

The patents, patent applications, references and other documents identified herein are incorporated in their entirety herein by reference.

EXAMPLES

It should be appreciated that the invention should not be construed to be limited to the examples now described; rather, the invention should be construed to include any and all applications provided herein and all equivalent variations within the skill of the ordinary artisan.

In reference to FIG. 2:

1. Central computer—This hosts the system main control software package and the database. The control software 1) reads the sample list, sends command to robotic freezer to get the correct plate, 2) controls the plate handler to deliver and delid the source plate by coordinating with the delid slide, 3) sends the source and destination positions to the picking robot, 4) controls dry nitrogen gas supply and 5) performs other detections and human machine interface operation.

2. Automatic Freezer—The BioPhile BSU stores the plates in the carousel inside, which is protected by dry N2 gas. It accepts retrieves and returns source plates through a robotic airtight port. It also has its own database for plate number management.

3. Transfer device—The Twister II can retrieve a plate with or without lid on. Its robotic arm can deliver the plate to various programmable positions. Its gripper is programmed for various forces to perform different actions such as lid removal when the lid sticks due to ice buildup.

4. Transfer device—Delid Slide—It moves along one axis. This allows the plate to be delidded, to have its barcode scanned, to be repositioned if necessary and to be located at positions corresponding to the desired column of a multiwell plate so that it is exposed to the access slot allowing the robot to pick the desired sample. This is a commercial slider modified with a custom delidding frame.

5. Addressable sampler (picking Robot)—This is an industrial precision robot (Adept Cobra). It can access a wide working space rapidly. It can be equipped with different functional heads. It can also work with a visual system.

6. Tip Head—This is designed for reliable tip handling. It has spring compensation for different plate types to compensate for variable sample height in different sample wells. It also provides a gentle and constant downwards force as the tip thaws the sample. It has a magnetic tip holder that provides constant temperature control for the tip as well.

7. Robot Controller—This is the controller dedicated to the picking robot. It provides digital control for other detection and valve controls.

8. Rotating Tip Station—It has 4 positions for tips. When it rotates, the tip at position #1 will go through the sterilization process by being positioned above the hot air gun. Positions 2, 3 and 4 are ambient air cooling stations; position 4 is the pickup station. The motor is on a constant dwell time, currently calibrated at 20 seconds. This dwell time can be calibrated to adjust average tip temperature if necessary.

9. Tips—These are metal tips with high thermal capacity. They are spring loaded to ensure reliable release from the tip head.

10. Tip Heat Sensor—This device monitors the hot air temperature in the vicinity of the pin at position 1 of the tip station. This allows the system to determine if the pin has warmed to the correct temperature to automatically transition the system from standby/warmup phase to picking phase.

11. Ethanol Well—Two wells hold 70% ethanol or other solvents for sterilization. The robot dips the used tip in the well(s) prior to heat sterilization. This was found to give more reliable sterilization than heat alone.

12. $N_2$ Control Valve/lid dryer—It controls dry $N_2$ injection to the Environmental Transfer chamber to minimize consumption of protective dry, sterile $N_2$ gas. The $N_2$ gas is directed at the underside of the lid holder that holds the current source plate lid, reducing ice buildup on the lid.

13. $N_2$ Environmental Transfer Chamber—It encloses the plate handler, delid slide, and barcode reader. It interfaces with the port of the robotic freezer. It can also be extended to interface with multiple freezers.

14. Frozen Sample Plate—This is the multi-well source plate. It is typically sealed with foil and covered by a loose fitting plate lid, and is labeled with a unique barcode for identification tracking. The sample information is stored in a database.

15. Destination Plate—There are one or more plates to accept the sample(s) delivered by picking robot.

16. Hot Air Gun—It heats up the tip to sterilize and/or dry the tip. Currently temperatures of 200-350° C. are used.

17. Network Router—It links the major devices in the system for reliable and quick operation.

18. Barcode Scanner—It reads the barcode for each plate. This information is used for ID validation when retrieving the plates.

19. Carousel—It sits inside the freezer and serves as the hotel for plates.

20. Dispensing Port—It is an air tight port which receives and releases plate.

Operation Procedure:

Step 1: Check the following issues before starting System software.

1) Power off "TRANSPORT POWER" if necessary.
2) Open the chamber cover; check the plate holder on the transport rail with the spacer for ZERO position.
3) Power on "TRANSPORT POWER".
4) Cover the chamber.
5) Turn Nitrogen manual valve on. Check the Biophile with "Biophile CommTest1" on the desktop if necessary. Perform "AAA", "H", "R" in sequence.

Step 2: Prepare the "hit list"

1) Go to E:\Order and open Genlist.xls with Macro enable.
2) Click "Load Order" to input the hit list in Excel file which is in the proper template format.
3) Chose the destination plate format: 96 or 384-well.
4) Click "Generate List"
5) Copy column M, paste to ConTEXT and save as text file.
6) Notice the format of the list: "IOH 10003; UH A 87; 96; 3; 1; JH B 8000; 384; 1; 1; 3"—[Gene ID; Source Plate Barcode; Plate format (96/384); Row; Column; Destination plate; Plate format (96/384); Plate position (1-4); Row; Column]. The 1st line is the title.

Step 3: Prepare working conditions
1) Clean up the working surface. Move away any extraneous materials from the work table.
2) Replace the fresh 70% ethanol in the 6-well plate.
3) Turn Hot Air Gun power on.
4) Check that all four tips are in good condition and in place on the rotating tip station. If necessary, sterilize tips first.
5) Turn on the $N_2$ valve.

Step 4: Start Adept robot
1) Turn the "ROBOT POWER" on if necessary.
2) Run "AdeptWindowsPC" from Start.
3) IP address 172.16.180.108
4) Note: if the Adept is POWER OFF, the AdeptWindowsPC software has to be started 5 seconds later right after POWER ON. It is not necessary to turn off ROBOT POWER for daily operation.
5) DDT prompt "Load from local disk (D) or network disk (X) [default is D]?" Select default.
6) Release any emergency button on the control pendant.
7) Press "COMP/PWR" and white button to power on robot.
8) Type "Calibrate" and confirm with "Y".
9) Load program for Adept from networking disk in PC "load nfs>xc:\ice\mainpicking.v2"
10) If program exists, either keep it or clean it with "zero"+ "Y"
11) Turn the tip heater ON.
12) Run "ex mainpicking"
13) Check that the proper number and type of destination plates, filled with appropriate media formulation, are in place.

Step 5: Start PC Software
1) Click SystemNet on desktop.
2) "Reset System"—Reset devices which includes Biophile, Twister II
3) "Load List"—Load the text file generated in step 2.
4) "Start Picking"
5) Tip Temperature >45 C, (This is the average temperature in the picking tip area above the heat gun. The tip temperature should be >150 C. The heat gun should be set to 250° C. for yeast. Use 300° C. for bacteria.). Program will pause sequence until proper temperature is reached.

Step 6: Finish day's operation
1) Turn $N_2$ valve off to conserve gas.
2) Clean the table.

Database Manipulation

Sometime, it is necessary to manipulate the database for the Biophile. For example, in case you have to unload all plates from the freezer manually to defrost the freezer. Only authorized people can perform these functions.
1) Go My Network Places.
2) BIOPHILE on Biophile, user name "Administrator", No Password
3) \Genone\Database\bflFreezerData, type the password.
Maintenance
Part 1: BioPhile Every time you open the door of BioPhile, you have a lot of problems to solve. One big headache is that you may not be able to home the robots inside the BioPhile.
1) Unload all plates to backup −80° C. freezer.
2) Leave door open and thaw Biophile overnight.
3) Unplug to power off completely including UPS.
4) Rotate the lift all the way up to the limit and back off a few turns.
5) Check the black registration marks for the lift and carousel.
6) Close the door.
7) "H" to home the Biophile.

8) If any plate location is damaged, change the database to mark location as unavailable.

Estimation of Volume Transferred Per Picking Operation

Starting material: LB+10% glycerol in 384 well plate. Plate type: 384-well low profile (Genetix) Total starting volume per well: 50 µL.

A picking pin was inserted by hand into the well and transferred to a piece of blotting paper. Liquid transfer was visible as a spot of liquid for 51 sequential picks. After this point, no further liquid could be transferred. Therefore the average volume transferred per pick from a 384 well source plate is approximately 1 µL.

Reproducibility of Viable Cell Transfers, Lack of Cross Contamination, and Estimate of Number of Viable Cells Transferred on Picking Tip.

Starting materials, loaded into BioPhile BSU: Saturated cultures of *Escherichia coli* "DH10B-T1" strain containing an Ultimate ORF® clone from Invitrogen Corporation (in LB+50 micGm/ml kanamycin+10% [w/v] glycerol) and *Saccharomyces cerevisiae* strain 4741 ho::kanMX (in YPD medium+200 micGm/ml G418+10% [w/v] glycerol). These cultures were grown in 96 well plate wells (low-profile Genetix plates) in 150 µL to saturation at 30° C. The cultures were each diluted 10-fold, 100-fold and 1000-fold into the appropriate medium as defined above. These source plates were covered with sterile foil seals, as well as the plastic lid, and then frozen at −80° C. by placing them in the BioPhile. The concentration of viable cells in the undiluted starting cultures was approximately as follows.

*S. cerevisiae*
$10^8$ cells per mL
or $10^5$ cells per µL
*E. coli*
$10^9$ cells per mL
or $10^6$ cells per µL The destination plates contained the appropriate growth medium. They were left open to the air during the entire picking operation. No special procedures were used to minimize airborne contamination. For example, the room air was not HEPA filtered, and the IcePick area was not sterilized with a germicidal lamps between picking runs. These simple procedures are predicted to further minimize airborne contamination.

Figure 10B:
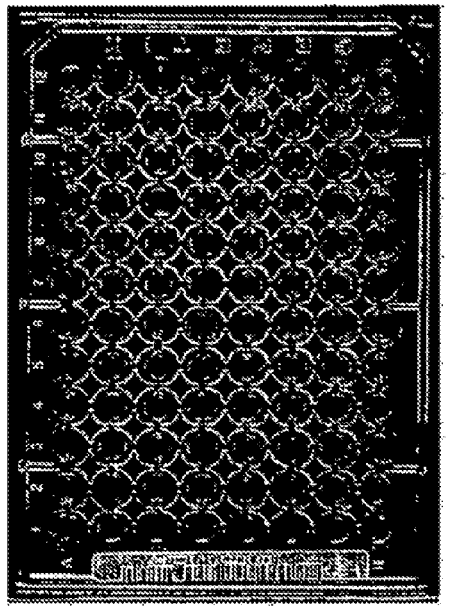
FIG. 10B shows bacterial *E. coli* plates.
Figure 10A:
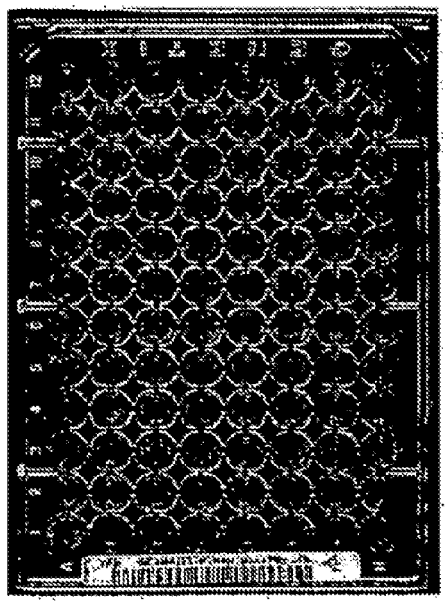
FIG. 10A shows yeast *S. cerevisiae* plates.
Figure 10C:
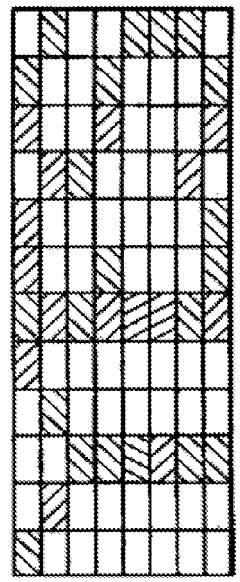
FIG. 10C shows "heat map" representation of bacterial growth as detected by a 96-well plate reader measuring A600. Blue represents background readings and shades of red represent different extents of growth.

FIGS. 10A, 10B, and 10C illustrate the results of cross contamination tests done with yeast and bacterial cells. Source plates with undiluted wells only and prepared as described were used. Destination plate wells were inoculated in a pattern spelling the word YES. As can be readily seen only these wells grew.

Figure 11B:
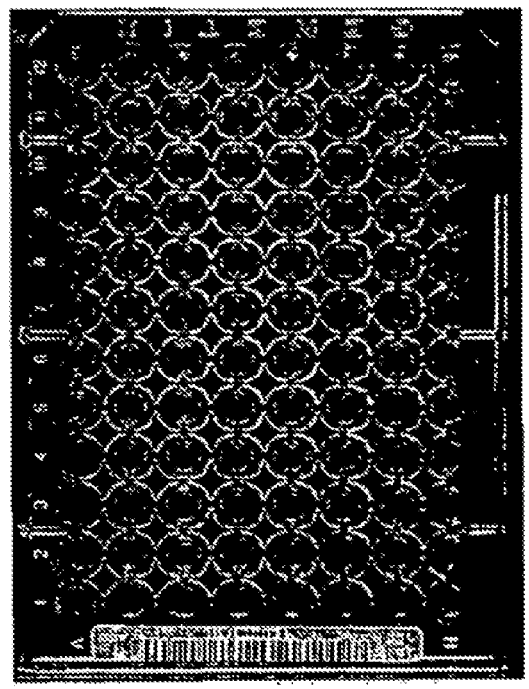
FIG. 11B shows bacterial *E. coli* plates.
Figure 11A:
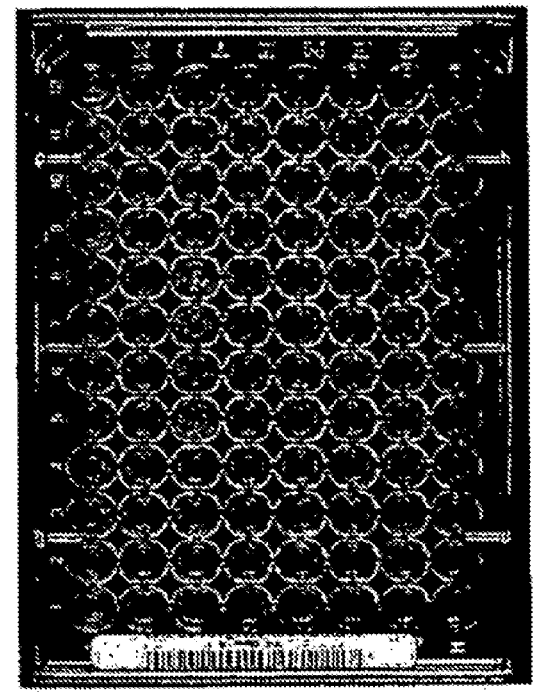
FIG. 11A depicts yeast *S. cerevisiae* plates.

FIG. 1A and 11B illustrate the results of the transfer experiment. Experiments are organized as follows: Wells A1-A4 are picked from four independent undiluted source wells, A9-A12 were picked from 10-fold diluted source wells, and C5-8 were picked from 100-fold diluted source wells. The remainder are blank wells to seek evidence of cross contamination. A5-A8 were touched by pins that were not dipped into source wells and the others were simply exposed to air during the entire picking operation, which lasted approximately 20 minutes.

FIGS. 10A, 10B, 10C, 11A, and 11B demonstrate that cross contamination is not detected using this procedure; importantly, this was true even though these experiments were performed without any special care taken to minimize contamination, such as lid closure on the destination plate during the picking time.

In reference to FIGS. 10A, 10B, and 10C, at least 10 cells/μL were viably transferred even at the highest source well dilution using this procedure.

What is claimed is:

1. A system for retrieving a subset of a stored sample, comprising:
    an automated freezer comprising a dispenser,
    a climate controlled receiving chamber adjacent to the dispenser,
    a transfer device within the receiving chamber,
    a robot operatively connected to the transfer device and positioned to access the subset of a stored sample,
    wherein the robot comprises a tip, said tip being selected from the group consisting of a metal tip with high thermal heat capacity, metal pin, a ceramic pin, a hollow pin, and a core sampler for retrieving a portion of a sample, and
    wherein the tip comprises a volume control mechanism.

2. The system of claim 1, wherein the dispenser communicates with the climate controlled receiving chamber through a port.

3. The system of claim 1, wherein the robot comprises a sample locator or a rotating tip station for maintaining sampling tips at a sampling temperature.

4. The system of claim 3, wherein the sample locator comprises a barcode reader.

5. The system of claim 1, further comprising a tip sterilizer positioned in functional proximity to the robot.

6. The system of claim 1, further comprising one or more destination plates for receiving retrieved samples positioned in functional proximity to the robot.

7. The system of claim 1, wherein the automated freezer is a vertical or horizontal storage freezer.

8. The system of claim 1, wherein the climate controlled receiving chamber comprises one or more of a humidity controller, an atmospheric gas control mechanism, a temperature controlling mechanism, or a reading device to identify the containers as they are inserted into and retrieved from the chamber.

9. A system for retrieving a subset of a stored sample, comprising:
    an automated freezer comprising a dispenser,
    a climate controlled receiving chamber adjacent to the dispenser,
    a transfer device within the receiving chamber,
    a robot operatively connected to the transfer device and positioned to access the subset of a stored sample, wherein the robot comprises a tip, and
    a heat sensor to monitor the temperature in the vicinity of the tip.

10. A system for retrieving a subset of a stored sample, comprising:
    an automated freezer comprising a dispenser,
    a climate controlled receiving chamber adjacent to the dispenser,
    a transfer device within the receiving chamber,
    a robot operatively connected to the transfer device and positioned to access the subset of a stored sample, and
    a delidder within the receiving chamber.

11. The system of claim 10, wherein the robot comprises a tip.

12. The system of claim 11, wherein the tip is selected from the group consisting of a metal tip with high thermal heat capacity, metal pin, a ceramic pin, a hollow pin, and a core sampler for retrieving a portion of a sample.

13. The system of claim 12, wherein the tip comprises a tip head.

14. The system of claim 12, wherein the tip is disposable.

15. A method for sampling a frozen sample, comprising:
    retrieving a sample in a container from a freezer,
    transferring the container to a climate controlled receiving chamber, and
    sampling the sample with a robot and transferring the container to the freezer.

16. The method of claim 15, further comprising delidding the container in the climate controlled chamber.

17. The method of claim 15, wherein retrieving the sample comprises ejecting the container to an exterior of the freezer for transport to the robot.

18. The method of claim 15, wherein sampling comprises transiently thawing at least a portion of the sample.

19. The method of claim 15, wherein the sample rapidly refreezes upon return to the freezer.

20. The method of claim 15, wherein the container comprises a multiwell plate.

21. The method of claim 20, wherein adjacent samples to the sample being sampled are not thawed.

22. The method of claim 15, further comprising sealing the container with a seal prior to freezing in the freezer a first time.

23. The method of claim 22, wherein the seal comprises a foil seal, a plastic seal, a polymer seal or a septum.

* * * * *